United States Patent
Ohyama et al.

(10) Patent No.: US 11,987,643 B2
(45) Date of Patent: May 21, 2024

(54) MONOCLONAL ANTIBODY THAT SPECIFICALLY BINDS TO SUGAR CHAIN IN WHICH TERMINAL SIALIC ACID RESIDUE IS BONDED TO GALACTOSE BY ALPHA 2,3 BOND, AND MEASUREMENT METHOD FOR SUGAR CHAIN IN WHICH TERMINAL SIALIC ACID RESIDUE IS BONDED TO GALACTOSE BY ALPHA 2,3 BOND

(71) Applicants: Hirosaki University, Aomori (JP); System Instruments Co., Ltd., Tokyo (JP)

(72) Inventors: Chikara Ohyama, Hirosaki (JP); Tohru Yoneyama, Hirosaki (JP); Kazuyuki Hamada, Oume (JP)

(73) Assignees: Hirosaki University, Aomori (JP); System Instruments Co., Ltd., Tokyo (JP)

( * ) Notice: Subject to any disclaimer, the term of this patent is extended or adjusted under 35 U.S.C. 154(b) by 0 days.

(21) Appl. No.: 17/918,042

(22) PCT Filed: Mar. 18, 2021

(86) PCT No.: PCT/JP2021/011034
§ 371 (c)(1),
(2) Date: Oct. 10, 2022

(87) PCT Pub. No.: WO2022/195796
PCT Pub. Date: Sep. 22, 2022

(65) Prior Publication Data
US 2024/0034811 A1    Feb. 1, 2024

(51) Int. Cl.
*C07K 16/44*    (2006.01)
*G01N 33/66*    (2006.01)

(52) U.S. Cl.
CPC ............ *C07K 16/44* (2013.01); *G01N 33/66* (2013.01); *C07K 2317/565* (2013.01)

(58) Field of Classification Search
CPC ... C07K 16/44; C07K 2317/565; G01N 33/66
See application file for complete search history.

(56) References Cited

U.S. PATENT DOCUMENTS

2015/0260720 A1    9/2015   Ohyama et al.

FOREIGN PATENT DOCUMENTS

| EP | 3410118 | 12/2018 |
|---|---|---|
| JP | IP-A-2002-055108 | 2/2002 |
| JP | B-4514919 | 7/2010 |
| JP | B-6381033 | 8/2018 |
| WO | WO 2014057983 | 4/2014 |
| WO | WO 2017130578 | 8/2017 |

OTHER PUBLICATIONS

Yoneyama, et al., "Measurement of aberrant glycosylation of prostate specific antigen can improve specificity in early detection of prostate cancer", Biochemical and Biophysical Research Communications, 448:390-396 (2014).
European Search Report issued in EP Application No. 21931547.0 dated Apr. 20, 2023.
Tajiri M, Ohyama C, Wada Y, Glycobiology, 2008; 18:2-8.
Chikara Ohyama, Is there a cancer-specific PSA ?: from sugar chain structure analysis of PSA, Urology View, Aug. 1, 2005, vol. 3, No. 4, 77-82 (English translation is not enclosed since an English translation of the ISR serves as a concise explanation of relevance).
International Search Report for PCT/JP2021/011034 dated May 18, 2021. (English translation attached).
Written Opinion of the International Search Authority for PCT/JP2021/011034 dated May 18, 2021. (English translation attached).

*Primary Examiner* — Changhwa J Cheu
(74) *Attorney, Agent, or Firm* — McDonnell Boehnen Hulbert & Berghoff LLP (57) ABSTRACT

A monoclonal antibody or an antibody fragment thereof is provided, in which the monoclonal antibody or the antibody fragment thereof specifically binds to a sugar chain in which a terminal sialic acid residue is bonded to galactose by an α2,3 bond, and is not dissociated from the sugar chain after the binding to the sugar chain in which the terminal sialic acid residue is bonded to the galactose by the α2,3 bond.α2,3

4 Claims, 5 Drawing Sheets
Specification includes a Sequence Listing.

SEQUENCE LISTING

```
<160> NUMBER OF SEQ ID NOS: 16

<210> SEQ ID NO 1
<211> LENGTH: 9
<212> TYPE: PRT
<213> ORGANISM: Oryctolagus cuniculus

<400> SEQUENCE: 1

Gly Phe Asp Leu Ser Asn Asn Tyr Val
1               5

<210> SEQ ID NO 2
<211> LENGTH: 9
<212> TYPE: PRT
<213> ORGANISM: Oryctolagus cuniculus

<400> SEQUENCE: 2

Ile Tyr Thr Gly Ser Ser Gly Ser Ala
1               5

<210> SEQ ID NO 3
<211> LENGTH: 19
<212> TYPE: PRT
<213> ORGANISM: Oryctolagus cuniculus

<400> SEQUENCE: 3

Ala Arg Gly Asp Val Phe Thr Arg Gly Gly Val Glu Tyr Ala Gly Val
1               5                   10                  15

Met Thr Leu

<210> SEQ ID NO 4
<211> LENGTH: 6
<212> TYPE: PRT
<213> ORGANISM: Oryctolagus cuniculus

<400> SEQUENCE: 4

Gln Ser Ile Ser Thr Ala
1               5

<210> SEQ ID NO 5
<211> LENGTH: 3
```

```
<212> TYPE: PRT
<213> ORGANISM: Oryctolagus cuniculus

<400> SEQUENCE: 5

Ser Ala Ser
1

<210> SEQ ID NO 6
<211> LENGTH: 13
<212> TYPE: PRT
<213> ORGANISM: Oryctolagus cuniculus

<400> SEQUENCE: 6

Gln Gly Tyr Asp Tyr Ile His Ser Arg Ala Asp Asn Ala
1               5                   10

<210> SEQ ID NO 7
<211> LENGTH: 9
<212> TYPE: PRT
<213> ORGANISM: Oryctolagus cuniculus

<400> SEQUENCE: 7

Gly Phe Ser Phe Ser Gly Ser Asp Trp
1               5

<210> SEQ ID NO 8
<211> LENGTH: 9
<212> TYPE: PRT
<213> ORGANISM: Oryctolagus cuniculus

<400> SEQUENCE: 8

Ile Tyr Ala Gly Ser Ser Gly Arg Thr
1               5

<210> SEQ ID NO 9
<211> LENGTH: 6
<212> TYPE: PRT
<213> ORGANISM: Oryctolagus cuniculus

<400> SEQUENCE: 9

Glu Arg Glu Val Asp Leu
1               5

<210> SEQ ID NO 10
<211> LENGTH: 7
<212> TYPE: PRT
<213> ORGANISM: Oryctolagus cuniculus

<400> SEQUENCE: 10

Gln Ser Val Tyr Ser Asn Tyr
1               5

<210> SEQ ID NO 11
<211> LENGTH: 3
<212> TYPE: PRT
<213> ORGANISM: Oryctolagus cuniculus

<400> SEQUENCE: 11

Gln Ala Ser
1

<210> SEQ ID NO 12
<211> LENGTH: 11
<212> TYPE: PRT
<213> ORGANISM: Oryctolagus cuniculus
```

-continued

<400> SEQUENCE: 12

Gln Gly Ala Tyr Ser Ser Gly Asp Gly Arg Ala
1               5                   10

<210> SEQ ID NO 13
<211> LENGTH: 125
<212> TYPE: PRT
<213> ORGANISM: Oryctolagus cuniculus

<400> SEQUENCE: 13

Gln Glu Gln Leu Glu Glu Ser Gly Gly Asp Leu Val Lys Pro Glu Gly
1               5                   10                  15

Ser Leu Thr Leu Thr Cys Thr Ala Ser Gly Phe Asp Leu Ser Asn Asn
                20                  25                  30

Tyr Val Met Cys Trp Val Arg Gln Ala Pro Gly Lys Gly Leu Glu Trp
            35                  40                  45

Ile Ala Cys Ile Tyr Thr Gly Ser Ser Gly Ser Ala Tyr Tyr Ala Ser
        50                  55                  60

Trp Pro Lys Gly Arg Phe Thr Ile Ser Lys Thr Ser Ser Thr Thr Val
65                  70                  75                  80

Thr Leu Gln Met Thr Ser Leu Thr Ala Ala Asp Thr Ala Thr Tyr Phe
                85                  90                  95

Cys Ala Arg Gly Asp Val Phe Thr Arg Gly Val Glu Tyr Ala Gly
            100                 105                 110

Val Met Thr Leu Trp Gly Pro Gly Thr Leu Val Thr Val
            115                 120                 125

<210> SEQ ID NO 14
<211> LENGTH: 114
<212> TYPE: PRT
<213> ORGANISM: Oryctolagus cuniculus

<400> SEQUENCE: 14

Ala Arg Cys Ala Leu Val Met Thr Gln Thr Ala Ser Pro Val Glu Ala
1               5                   10                  15

Ala Val Gly Gly Thr Val Thr Ile Lys Cys Gln Ala Ser Gln Ser Ile
                20                  25                  30

Ser Thr Ala Leu Ala Trp Tyr Gln Gln Lys Pro Gly Gln Pro Pro Lys
            35                  40                  45

Leu Leu Ile Tyr Ser Ala Ser Lys Leu Ala Ser Gly Val Pro Ser Arg
        50                  55                  60

Phe Ser Gly Ser Gly Ser Gly Thr Glu Phe Thr Leu Thr Ile Ser Gly
65                  70                  75                  80

Val Gln Cys Asp Asp Ala Ala Thr Tyr Tyr Cys Gln Gly Tyr Asp Tyr
                85                  90                  95

Ile His Ser Arg Ala Asp Asn Ala Phe Gly Gly Gly Thr Glu Val Val
            100                 105                 110

Val Lys

<210> SEQ ID NO 15
<211> LENGTH: 113
<212> TYPE: PRT
<213> ORGANISM: Oryctolagus cuniculus

<400> SEQUENCE: 15

Arg Ser Leu Glu Glu Ser Gly Gly Asp Leu Val Lys Pro Gly Ala Ser
1               5                   10                  15

```
Leu Thr Leu Thr Cys Thr Ala Ser Gly Phe Ser Phe Ser Gly Ser Asp
            20                  25                  30

Trp Ile Ser Trp Val Arg Gln Ala Pro Gly Lys Gly Leu Glu Trp Ile
            35                  40                  45

Ala Tyr Ile Tyr Ala Gly Ser Ser Gly Arg Thr Arg Tyr Ala Ser Trp
        50                  55                  60

Ala Lys Gly Arg Phe Thr Ile Ser Lys Thr Ser Ser Thr Val Thr
65                  70                  75                  80

Leu Gln Met Thr Ser Leu Thr Ala Ala Asp Thr Ala Thr Tyr Phe Cys
                85                  90                  95

Glu Arg Glu Val Asp Leu Trp Gly Pro Gly Thr Leu Val Thr Val Ser
                100                 105                 110

Ser

<210> SEQ ID NO 16
<211> LENGTH: 113
<212> TYPE: PRT
<213> ORGANISM: Oryctolagus cuniculus

<400> SEQUENCE: 16

Ala Thr Phe Ala Gln Val Val Thr Gln Thr Pro Ser Pro Val Ser Ala
1               5                   10                  15

Thr Leu Gly Gly Thr Val Thr Ile Asn Cys Gln Ser Ser Gln Ser Val
            20                  25                  30

Tyr Ser Asn Tyr Leu Ser Trp Phe Gln Gln Gln Pro Gly Gln Pro Pro
        35                  40                  45

Lys Leu Leu Met Tyr Gln Ala Ser Asn Leu Ala Ser Gly Val Pro Ser
        50                  55                  60

Arg Phe Lys Gly Ser Gly Ser Gly Thr Gln Phe Thr Leu Thr Ile Ser
65                  70                  75                  80

Ser Val Gln Cys Asp Asp Ala Ala Thr Tyr Tyr Cys Gln Gly Ala Tyr
                85                  90                  95

Ser Ser Gly Asp Gly Arg Ala Phe Gly Gly Gly Thr Glu Val Val Val
                100                 105                 110

Lys
```

MONOCLONAL ANTIBODY THAT SPECIFICALLY BINDS TO SUGAR CHAIN IN WHICH TERMINAL SIALIC ACID RESIDUE IS BONDED TO GALACTOSE BY ALPHA 2,3 BOND, AND MEASUREMENT METHOD FOR SUGAR CHAIN IN WHICH TERMINAL SIALIC ACID RESIDUE IS BONDED TO GALACTOSE BY ALPHA 2,3 BOND

This application is a U.S. National Phase application under 35 U.S.C. § 371 of PCT/JP2021/011034, filed on Mar. 18, 2021, the specification of which is hereby incorporated by reference in its entirety into the instant application.

TECHNICAL FIELD

The present invention relates to a monoclonal antibody that specifically binds to a sugar chain in which a terminal sialic acid residue is bonded to galactose by an α2,3 bond, and a measurement method for a sugar chain in which a terminal sialic acid residue is bonded to galactose by an α2,3 bond.

BACKGROUND ART

Regarding a sugar chain of prostate-specific antigen (PSA), which is a known marker for prostate cancer, it is known that a double-stranded N-type sugar chain in which sialic acid is bonded to galactose by an α2,6 bond at the terminal and an N-type sugar chain in which sialic acid at the terminal is bonded to galactose by an α2,3 bond are present, and that the number of sugar chains that are bonded to galactose by the α2,3 bond increases in association with canceration as compared with the α2,6 bond (Non-Patent Document 1). Accordingly, the detection of a sugar chain in which a terminal sialic acid residue is bonded to galactose by an α2,3 bond is useful for detecting prostate cancer.

Maackia amurensis Agglutinin (MAA) is a known probe capable of detecting a sugar chain in which a terminal sialic acid residue is bonded to galactose by an α2,3 bond, and it is used as a probe for detecting a sugar chain containing sialic acid (Patent Document 1). In addition, a mouse monoclonal antibody that recognizes a sugar chain in which a terminal sialic acid residue is bonded to galactose by an α2,3 bond has been reported where a glycolipid having a sugar chain in which a terminal sialic acid residue is bonded to galactose by an α2,3 bond is used as an immunogen (Patent Document 2).

Citation List

Patent Documents

[Patent Document 1]
  Japanese Patent No. 4514919
[Patent Document 2]
  Japanese Patent No. 6381033

Non-Patent Document

[Non-Patent Document 1]
  Tajiri M, Ohyama C, Wada Y, Glycobiology, 2008; 18: 2-8

DISCLOSURE OF INVENTION

Technical Problem

However, since Maackia amurensis Agglutinin is a natural product derived from a plant as a raw material and the binding property thereof changes depending on the lot of the product, the clinical application of a tumor biomarker using this as a probe is difficult. Although the development of recombinant lectins is underway, they have not yet been put into practical use.

In addition, an antibody that recognizes, with higher sensitivity, a sugar chain in which a terminal sialic acid residue is bonded to galactose by an α2,3 bond is required for the detection of cancerous PSA.

The present invention has been made in consideration of the above problems, and an object thereof is to provide a monoclonal antibody having a high binding property to a sugar chain in which a terminal sialic acid residue is bonded to galactose by an α2,3 bond, and a measurement method for a sugar chain in which a terminal sialic acid residue is bonded to galactose by an α2,3 bond.

Solution to Problem

The inventors of the present invention found that a monoclonal antibody obtained by immunizing a rabbit with Siaα2-3 Galβ1-4GlcNAc-BSA as an immunogen, isolating an obtained positive rabbit B cell, obtaining an antibody gene by single cell PCR, and introducing the antibody gene into a host cell binds to, with a high binding property, a sugar chain in which a terminal sialic acid residue is bonded to galactose by an α2,3 bond, and is not dissociated from the sugar chain after the binding to the sugar chain in which the terminal sialic acid residue is bonded to the galactose by the α2,3 bond, whereby the present invention was completed.

The present invention includes the following aspects.

[1] A monoclonal antibody or an antibody fragment thereof,
  wherein the monoclonal antibody or the antibody fragment thereof specifically binds to a sugar chain in which a terminal sialic acid residue is bonded to galactose by an α2,3 bond, and is not dissociated from the sugar chain after the binding to the sugar chain in which the terminal sialic acid residue is bonded to the galactose by the α2,3 bond.

[2] The monoclonal antibody or the antibody fragment thereof according to [1], in which a dissociation constant with the sugar chain in which the terminal sialic acid residue is bonded to the galactose by the α2,3 bond is $3.0 \times 10^{-8}$ or less.

[3] The monoclonal antibody or the antibody fragment thereof according to [1] or [2], in which the monoclonal antibody or the antibody fragment thereof does not bind to a sugar chain in which galactose to which sialic acid is not bonded is bonded to a terminal, or a dissociation constant with the sugar chain in which galactose to which the terminal sialic acid is not bonded is bonded is $9.0 \times 10^{-5}$ or more.

[4] The monoclonal antibody or the antibody fragment thereof according to any one of [1] to [3] in which an amino acid sequence of a complementarity-determining region (hereinafter, also referred to as CDR) 1 of a heavy chain variable region (hereinafter, also referred to as VH) of the antibody or the antibody fragment thereof includes an amino acid sequence set forth in SEQ ID NO: 1, an amino acid sequence of CDR2 of the VH includes an amino acid sequence set forth in SEQ ID NO: 2, an amino acid sequence of CDR3 of VH includes an amino acid sequence set forth in SEQ ID NO:3, an amino acid sequence of CDR1 of a light chain variable region (hereinafter, also referred to as VL) includes an amino acid sequence set forth in SEQ ID NO:4, an amino acid sequence of CDR2 of VL includes an amino acid sequence set forth in SEQ ID NO: 5, and an amino acid sequence of CDR3 of VL includes an amino acid sequence set forth in SEQ ID NO: 6.

[5] The monoclonal antibody or the antibody fragment thereof according to [4], in which an amino acid sequence of the VH of the antibody or the antibody fragment thereof includes an amino acid sequence set forth in SEQ ID NO: 13, and an amino acid sequence of VL includes an amino acid sequence set forth in SEQ ID NO: 14.

[6] The monoclonal antibody or the antibody fragment thereof according to any one of [1] to [3], in which an amino acid sequence of CDR3 of VH of the antibody or the antibody fragment thereof includes an amino acid sequence set forth in SEQ ID NO: 9, and an amino acid sequence of CDR3 of VL includes an amino acid sequence set forth in SEQ ID NO: 12.

[7] The monoclonal antibody or the antibody fragment thereof according to [6], in which an amino acid sequence of CDR1 of the VH of the antibody or the antibody fragment thereof includes an amino acid sequence set forth in SEQ ID NO: 7, an amino acid sequence of CDR2 of the VH includes an amino acid sequence set forth in SEQ ID NO: 8, the amino acid sequence of CDR3 of VH includes an amino acid sequence set forth in SEQ ID NO: 9, an amino acid sequence of CDR1 of VL includes an amino acid sequence set forth in SEQ ID NO: 10, an amino acid sequence of CDR2 of VL includes an amino acid sequence set forth in SEQ ID NO: 11, and the amino acid sequence of CDR3 of VL includes an amino acid sequence set forth in SEQ ID NO: 12.

[8] The monoclonal antibody or the antibody fragment thereof according to [7], in which an amino acid sequence of the VH of the antibody or the antibody fragment thereof includes an amino acid sequence set forth in SEQ ID NO: 15, and an amino acid sequence of VL includes an amino acid sequence set forth in SEQ ID NO: 16.

[9] A measurement method for a sugar chain in which a terminal sialic acid residue is bonded to galactose by an α2,3 bond, the measurement method including using the monoclonal antibody or the antibody fragment thereof according to any one of [1] to [8].

Advantageous Effects of Invention

According to the present invention, it is possible to provide a monoclonal antibody having a high binding property to a sugar chain (hereinafter, also referred to as an α2,3 sugar chain) in which a terminal sialic acid residue is bonded to galactose by an α2,3 bond, and a measurement method for an α2,3 sugar chain.

BEST MODE FOR CARRYING OUT THE INVENTION

Hereinafter, embodiments according to the present invention will be described in detail.

Monoclonal Antibody and Antibody Fragment Thereof

In the present specification, the "antibody" in the present specification refers to a full-length immunoglobulin molecule that exists in nature or is produced by genetic recombination technology, and the "antibody fragment" refers to an antigen-binding fragment of such an immunoglobulin molecule. Such an antibody and antibody fragment can be prepared using a conventional technology. Examples of the antibody fragment include F(ab')$_2$, F(ab)$_2$, Fab', Fab, Fv, scFv, variants thereof, a fusion protein or peptide including an antibody portion, and a modified structure other than an immunoglobulin molecule including an α2,3 sugar chain-binding site.

In the present invention, the description that an antibody "specifically binds" means that the antibody substantially does not bind to a sugar chain that is different from the sugar chain in which a terminal sialic acid residue is bonded to galactose by an α2,3 bond but binds to an α2,3 sugar chain. Further, in the present specification, the "α2,3 sugar chain" is also referred to as "Siaα2-3Galβ1-4GlcNAc".

In the present invention, the "monoclonal antibody" means an antibody obtained from a substantially homogeneous population, and an individual antibody contained in the population is identical except for possible natural mutants that may be present. The monoclonal antibody is an antibody exhibiting one binding specificity and affinity for a specific epitope of an antigen. The modifier "monoclonal" indicates the properties of the antibody obtained from a substantially homogeneous antibody population, and it is not to be construed as being limited by requiring production of the antibody by a specific method.

The "heavy chain" of an antibody, used in the present specification, refers to a larger one of the two types of polypeptide chains present in all antibody molecules in a conformation present in nature. The "light chain" of an antibody used in the present specification refers to a smaller one of the two types of polypeptide chains present in all antibody molecules in a conformation present in nature.

Here, the complementarity-determining region (CDR) is composed of a heavy chain complementarity-determining region and a light chain complementarity-determining region. Each of the variable regions of the heavy chain and the light chain consists of three CDRs and four framework regions (FRs) connected by the CDRs. The CDRs in each chain are held in the vicinity by the FRs, and contribute to the formation of an antigen-binding site of the antibody, together with the CDRs in other chains.

Technologies for determining CDRs include, but are not limited to, (1) an approach based on heterologous sequence variability (for example, Kabat et al. Sequences of Proteins of Immunological interest, 5th ed., 1991, National Institutes of Health, Bethesda MD); and (2) an approach based on crystallographic studies of the antigen-antibody complex (Al-lazikani et al., J. Molec. Biol. 273, 927-948, 1997), for example. These and other approaches may be used in combination.

The monoclonal antibody or the antibody fragment thereof according to the present invention is a monoclonal antibody or an antibody fragment thereof which specifically binds to an α2,3 sugar chain and is not dissociated from the sugar chain after the binding to the α2,3 sugar chain. Hereinafter, the monoclonal antibody according to the present invention is also referred to as an anti-α2,3 sugar chain monoclonal antibody.

The anti-α2,3 sugar chain monoclonal antibody according to the present invention may be a human antibody or may be a non-human animal antibody. Examples of the non-human animal include a mouse, a rat, a hamster, a rabbit, a goat, a sheep, and a chicken, where a rabbit monoclonal antibody is preferable since it has a high binding property to an antigen.

The anti-α2,3 sugar chain monoclonal antibody or the antibody fragment thereof according to the present invention is preferably a monoclonal antibody or an antibody fragment thereof which does not bind to an α2,6 sugar chain.

The binding property of the anti-α2,3 sugar chain monoclonal antibody or the antibody fragment thereof according to the present invention to an antigen such as an α2,3 sugar chain or an α2,6 sugar chain can be indicated by a dissociation constant (a KD value). The unit of KD is M, and the higher the binding property, the lower the KD value.

The KD value of the anti-α2,3 sugar chain monoclonal antibody or the antibody fragment thereof according to the present invention with the α2,3 sugar chain is preferably $3.0 \times 10^{-8}$ or less, more preferably $2.7 \times 10^{-8}$ or less, still more preferably $2.5 \times 10^{-8}$ or less, and particularly preferably $2.0 \times 10^{-8}$ or less.

The KD value can be calculated using, for example, a biosensor on which a sugar chain acting as an antigen is immobilized. Specifically, a sugar chain acting as an antigen is immobilized on a biosensor and immersed in an antibody solution to allow the antibody to bind to the antigen immobilized on the biosensor. Then, the biosensor is immersed in a buffer solution such as phosphate-buffered saline (PBS), the change in the wavelength shift Δλ caused by the change in the number of antibodies bound to the biosensor or the number of antibodies dissociated from the biosensor is measured, and then the KD value can be calculated from the sensorgram obtained when the concentration of the antibody is changed.

The anti-α2,3 sugar chain monoclonal antibody or the antibody fragment thereof according to the present invention is not dissociated from the sugar chain after binding to the sugar chain in which the terminal sialic acid residue is bonded to the galactose by the α2,3 bond. The fact that the anti-α2,3 sugar chain monoclonal antibody or the antibody fragment thereof according to the present invention is not dissociated from the sugar chain after the binding to the α2,3 sugar chain can be confirmed by the above-described biosensor. Specifically, the monoclonal antibody or the antibody fragment thereof according to the present invention is bound to an α2,3 sugar chain immobilized on a biosensor, and then the biosensor is immersed in a buffer solution containing no α2,3 sugar chain to obtain a reaction profile showing the binding to and dissociation from the α2,3 sugar chain, from which the above fact can be confirmed. In a case where the anti-α2,3 sugar chain monoclonal antibody or the antibody fragment thereof according to the present invention is bound to the α2,3 sugar chain immobilized on the biosensor, it is not dissociated from the α2,3 sugar chain immobilized on the biosensor even in a case of being immersed in a buffer solution containing no α2,3 sugar chain. On the other hand, even in a case where the anti-α2,3 sugar chain monoclonal antibody or the antibody fragment thereof according to the present invention is bound to a sugar chain other than the α2,3 sugar chain immobilized on the biosensor, for example, an α2,6 sugar chain, it is rapidly dissociated from the α2,6 sugar chain immobilized on the biosensor in a case of being immersed in a buffer solution containing no α2,6 sugar chain. Accordingly, even in a case where the α2,6 sugar chain is bound to the anti-α2,3 sugar chain monoclonal antibody or the antibody fragment thereof according to the present invention, it is replaced with the α2,3 sugar chain in a case where the α2,3 sugar chain is present. As a result, the anti-α2,3 sugar chain monoclonal antibody or the antibody fragment thereof according to the present invention has high specificity to the α2,3 sugar chain even in a case where the KD value with the α2,3 sugar chain is high and the KD value with the α2,6 sugar chain is low.

The anti-α2,3 sugar chain monoclonal antibody or the antibody fragment thereof according to the present invention is preferably a monoclonal antibody or an antibody fragment thereof which does not bind to a galactose-bonded sugar chain or hardly binds to a galactose-bonded sugar chain. Here, examples of the monoclonal antibody or the antibody fragment thereof which hardly binds to a galactose-bonded sugar chain include a monoclonal antibody or an antibody fragment thereof which has a dissociation constant (a KD value) with the galactose-bonded sugar chain of $9.0 \times 10^{-5}$ or more.

The anti-α2,3 sugar chain monoclonal antibody or the antibody fragment thereof according to the present invention can be produced by using a known method. Specifically, first, a conjugate of an α2,3 sugar chain and a carrier protein is used as an immunogen to immunize a non-human animal, the binding property to an antigen is checked by ELISA for lymphocytes of the immunized non-human animal, and then a lymphocyte having a high binding property to the α2,3 sugar chain is selected. Examples of the non-human animal to be immunized include a mouse, a rat, a hamster, a rabbit, a goat, sheep, and a chicken. Next, the antibody gene is obtained from the selected lymphocyte by the single cell PCR method and amplified by the PCR method. For the PCR amplification product, the binding property to the antigen is confirmed by ELISA. A PCR amplification product having a high binding property to the α2,3 sugar chain is transfected into cells such as human embryonic kidney cells 293, the culture supernatant containing the secreted antibody is recovered, and the binding property of the recovered sample to the antigen is confirmed by ELISA, thereby obtaining a clone having a high binding property to the α2,3 sugar chain. The antibody gene is obtained from the obtained clone and inserted into a vector to obtain an antibody-producing cell. The obtained antibody-producing cell is cultured to generate and accumulate the anti-α2,3 sugar chain monoclonal antibody or the antibody fragment thereof according to the present invention, and the anti-α2,3 sugar chain monoclonal antibody or the antibody fragment thereof according to the present invention can be produced from the culture.

The anti-α2,3 sugar chain monoclonal antibody or the antibody fragment thereof according to the present invention includes an anti-α2,3 sugar chain monoclonal antibody No. 14 (hereinafter, also referred to as a No. 14 antibody) or an antibody fragment thereof which includes an amino acid sequence of CDR1 of VH including an amino acid sequence set forth in SEQ ID NO: 1, an amino acid sequence of CDR2 of the VH including an amino acid sequence set forth in SEQ ID NO: 2, an amino acid sequence of CDR3 of VH including an amino acid sequence set forth in SEQ ID NO: 3, an amino acid sequence of CDR1 of VL including an amino acid sequence set forth in SEQ ID NO: 4, an amino acid sequence of CDR2 of VL including an amino acid sequence set forth in SEQ ID NO: 5, and an amino acid sequence of CDR3 of VL including an amino acid sequence set forth in SEQ ID NO: 6.

The antibody No. 14 includes VH including an amino acid sequence set forth in SEQ ID NO: 13 and VL including an amino acid sequence set forth in SEQ ID NO: 14.

Further, the anti-α2,3 sugar chain monoclonal antibody or the antibody fragment thereof according to the present invention includes an anti-α2,3 sugar chain monoclonal antibody or an antibody fragment thereof in which an amino acid sequence of CDR3 of VH of the antibody or the antibody fragment thereof includes an amino acid sequence set forth in SEQ ID NO: 9, and an amino acid sequence of VL includes an amino acid sequence set forth in SEQ ID NO: 12.

Specific examples of the anti-α2,3 sugar chain monoclonal antibody or the antibody fragment thereof in which an amino acid sequence of CDR3 of VH includes an amino acid sequence set forth in SEQ ID NO: 9, and an amino acid sequence of VL includes an amino acid sequence set forth in SEQ ID NO: 12, include an anti-α2,3 sugar chain monoclonal antibody No. 19 (hereinafter, also referred to as a No. 19 antibody) or an antibody fragment thereof which includes an amino acid sequence of CDR1 of VH including an amino acid sequence set forth in SEQ ID NO: 7, an amino acid sequence of CDR2 of the VH including an amino acid sequence set forth in SEQ ID NO: 8, an amino acid sequence of CDR3 of VH including an amino acid sequence set forth in SEQ ID NO: 9, an amino acid sequence of CDR1 of VL including an amino acid sequence set forth in SEQ ID NO: 10, an amino acid sequence of CDR2 of VL including an amino acid sequence set forth in SEQ ID NO: 11, and an amino acid sequence of CDR3 of VL including an amino acid sequence set forth in SEQ ID NO: 12.

The antibody No. 19 includes VH including an amino acid sequence set forth in SEQ ID NO: 15 and VL including an amino acid sequence set forth in SEQ ID NO: 16.

The amino acid sequences set forth in SEQ ID NO: 1 to SEQ ID NO:12 are shown in Table 1.

TABLE 1

| Antibody No. | SEQ ID | Variable region | CDR | Amino acid sequence |
|---|---|---|---|---|
| 14 | 1 | VH | 1 | GFDLSNNYV |
|  | 2 | VH | 2 | IYTGSSGSA |
|  | 3 | VH | 3 | ARGDVFTRGGVEY-AGVMTL |
|  | 4 | VL | 1 | QSISTA |
|  | 5 | VL | 2 | SAS |
|  | 6 | VL | 3 | QGYDYIHSRADNA |
| 19 | 7 | VH | 1 | GFSFSGSDW |
|  | 8 | VH | 2 | IYAGSSGRT |
|  | 9 | VH | 3 | EREVDL |
|  | 10 | VL | 1 | QSVYSNY |
|  | 11 | VL | 2 | QAS |
|  | 12 | VL | 3 | QGAYSSGDGRA |

The amino acid sequences set forth in SEQ ID NO: 13 to SEQ ID NO:16 are shown in Table 2.

TABLE 2

| Antibody No. | SEQ ID | Variable region | Amino acid sequence |
|---|---|---|---|
| 14 | 13 | VH | QEQLEESGGDLVKPEGSLTLTCTASGFDLSNNYVMCWVRQAPGK GLEWIACIYTGSSGSAYYASWPKGRFTISKTSSTTVTLQMTSLTAA DTATYFCARGDVFTRGGVEYAGVMTLWGPGTLVTV |
|  | 14 | VL | ARCALVMTQTASPVEAAVGGTVTIKCQASQSISTALAWYQQKPG QPPKLLIYSASKLASGVPSRFSGSGSGTEFTLTISGVQCDDAATYY CQGYDYIHSRADNAFGGGTEVVVK |
| 19 | 15 | VH | RSLEESGGDLVKPGASLTLTCTASGFSFSGSDWISWVRQAPGKGL EWIAYIYAGSSGRTRYASWAKGRFTISKTSSTTVTLQMTSLTAADT ATYFCEREVDLWGPGTLVTVSS |
|  | 16 | VL | ATFAQVVTQTPSPVSATLGGTVTINCQSSQSVYSNYLSWFQQQP GQPPKLLMYQASNLASGVPSRFKGSGSGTQFTLTISSVQCDDAA TYYCQGAYSSGDGRAFGGGTEVVVK |

The anti-α2,3 sugar chain monoclonal antibody according to the present invention or an antibody fragment thereof which includes CDR1 to CDR3 of VH and CDR1 to CDR3 of VL can be produced by using a known genetic recombination technology. Specifically, it is possible to produce this antibody or the antibody fragment thereof by incorporating each of the genes encoding CDR1 to CDR3 of VH and CDR1 to CDR3 of VL into a vector including each of the FR of the antibody and the gene encoding the constant region of the antibody, introducing this into a host cell, and transforming the host cell to obtain a cell expressing the antibody, and culturing the cell. The cell used in the preparation, the kind of the vector, the kind of the cell, the culture conditions, and the like are within the technical range of those skilled in the art, and appropriate conditions can be appropriately set.

The monoclonal antibody or the antibody fragment thereof according to the present invention also includes a monoclonal antibody or an antibody fragment thereof in which in the amino acid sequences of CDR1 to 3 of VH and VL one or more amino acids are deleted, added, substituted, or inserted and which has the same specificity as the monoclonal antibody or the antibody fragment thereof according to the present invention.

The number of amino acids to be deleted, substituted, inserted, and/or added is one or more, and the number thereof is not particularly limited; however, it is such a number that deletion, substitution, or addition can be carried out by a well-known technique such as a site-specific mutagenesis method [Molecular Cloning 2nd Edition, Cold Spring Harbor Laboratory Press (1989), Current Protocols in molecular Biology, John Wiley & Sons (1987-1997), Nucleic Acids Research 10, 6487 (1982), Proc. Natl. Acad. Sci. USA, 79, 6409 (1982), Gene, 34, 315 (1985), Nucleic Acids Research, 13, 4431 (1985), Proc. Natl. Acad. Sci. USA, 82, 488 (1985)]. For example, it is preferably 1 to several tens of amino acids, more preferably 1 to 20 amino acids, still more preferably 1 to 10 amino acids, and particularly preferably 1 to 5 amino acids.

Measurement Method

The measurement method for an α2,3 sugar chain according to the present invention is a measurement method for an α2,3 sugar chain, using the anti-α2,3 sugar chain monoclonal antibody or the antibody fragment thereof according to the present invention. Examples of the measurement method for an α2,3 sugar chain, using the anti-α2,3 sugar chain monoclonal antibody or the antibody fragment thereof according to the present invention include an immunological measurement method for an α2,3 sugar chain in a specimen in which an α2,3 sugar chain in a specimen is reacted with the anti-α2,3 sugar chain monoclonal antibody or the antibody fragment thereof according to the present invention, a labeled antibody or a labeled antibody fragment, having a label bound to the anti-α2,3 sugar chain monoclonal antibody or the antibody fragment thereof is subsequently added to generate an immune complex consisting of the α2,3 sugar chain, the anti-α2,3 sugar chain monoclonal antibody or the antibody fragment thereof, and the labeled antibody or the labeled antibody fragment, and the amount of the label in the generated immune complex is measured.

In the measurement method using the anti-α2,3 sugar chain monoclonal antibody or the antibody fragment thereof according to the present invention, examples of the specimen include blood such as serum, plasma or whole blood, lymphatic fluid, tissue fluid, cerebrospinal fluid, body cavity fluid, digestive juice, nasal secretions, tears, sweat, and urine of animals including a human. Furthermore, the specimen may be the specimen itself collected from a subject, or a product obtained by subjecting the collected specimen to treatments such as dilution and concentration, which are usually carried out. In addition, the specimen may be a specimen collected or prepared at the time of carrying out the measurement method or may be a specimen collected or prepared in advance and stored.

The immunological measurement method can be classified into an enzyme immunoassay (EIA or ELISA), a radioimmunoassay (RIA), a fluorescence immunoassay (FIA), a fluorescence polarization immunoassay (FPIA), a chemiluminescence immunoassay (CLIA), electrochemiluminescence immunoassay, or the like depending on the label of the labeled detection antibody, and any one of these can be used in the measurement method according to the present invention. However, ELISA is preferable since it is possible to conveniently and quickly measure the detection subject.

The α2,3 sugar chain in the specimen can be measured by washing the immune complex and then measuring the label in the immune complex. For example, in a case of ELISA, the α2,3 sugar chain in the specimen can be measured by reacting an enzyme, which is a label, with a substrate of the enzyme and measuring the absorbance of a colored product (a sandwich method). Furthermore, the α2,3 sugar chain in the specimen can also be measured by reacting the anti-α2,3 sugar chain monoclonal antibody or the antibody fragment thereof according to the present invention immobilized on a solid support with the α2,3 sugar chain in the specimen, subsequently adding an unlabeled anti-α2,3 sugar chain monoclonal antibody or an antibody fragment thereof (a primary antibody), further adding a labeled secondary antibody obtained by labeling an antibody (a secondary antibody) against this unlabeled sugar chain antibody or the antibody fragment thereof with enzyme, and measuring the label of the secondary antibody. In addition, the α2,3 sugar chain in the specimen can be measured by labeling the secondary antibody with biotin, allowing avidin or streptavidin labeled with an enzyme or the like to bind to biotin, labeling the secondary antibody with an enzyme and the like, and measuring the label of the secondary antibody.

The α2,3 sugar chain in the specimen can also be measured by adding an unlabeled anti-α2,3 sugar chain monoclonal antibody or an antibody fragment thereof (a primary antibody) to an α2,3 sugar chain or a conjugate of an α2,3 sugar chain and a protein such as BSA immobilized on a solid support to generate an immune complex consisting of the α2,3 sugar chain and the primary antibody on the solid support, adding the specimen, further adding a labeled secondary antibody obtained by labeling an antibody (a secondary antibody) against this unlabeled antibody, and measuring the label of the labeled secondary antibody (a competitive method).

The solid support is not particularly limited as long as the solid support can reliably hold an antibody or an antibody fragment. Examples of the preferred material of the solid support include polymer materials such as polystyrene, polycarbonate, polyvinyl toluene, polypropylene, polyethylene, polyvinyl chloride, nylon, polymethacrylate, gelatin, agarose, cellulose, nitrocellulose, cellulose acetate, acetyl cellulose, and polyethylene terephthalate, glass, ceramics, magnetic particles, metal. Examples of the preferred shape of the solid support include fine particles such as a tube, a bead, a plate, and latex, sticks.

As the label, it is possible to use an enzyme such as peroxidase and alkaline phosphatase in ELISA, a radioactive substance such as $^{125}I$, $^{131}I$, $^{35}S$, and $^{3}H$ in the RIA method, and a fluorescent substance such as fluorescein isothiocyanate, rhodamine, dansyl chloride, phycoerythrin, tetramethyl rhodamine isothiocyanate, and a near-infrared fluorescent material in the FPIA method, an enzyme such as luciferase and β-galactosidase and a luminescent substrate that is converted into a luminescent substance by each enzyme, and a luminescent substance such as luciferin and aequorin in the CLIA method. In addition, nanoparticles such as colloidal gold and quantum dots can be used as labels.

In ELISA, as the substrate of the enzyme which serves as a label, in a case where the enzyme is peroxidase, 3,3'-diaminobenzidine (DAB), 3,3',5,5'-tetramethylbenzidine (TMB), O-phenylenediamine (OPD), and the like can be used, and in a case where the enzyme is alkaline phosphatase, p-nitrophenyl phosphate (pNPP) and the like can be used.

EXAMPLES

Hereinafter, the present invention will be described in more detail with reference to Examples; however, the present invention is not limited to these Examples.

Example 1

Figure 1:
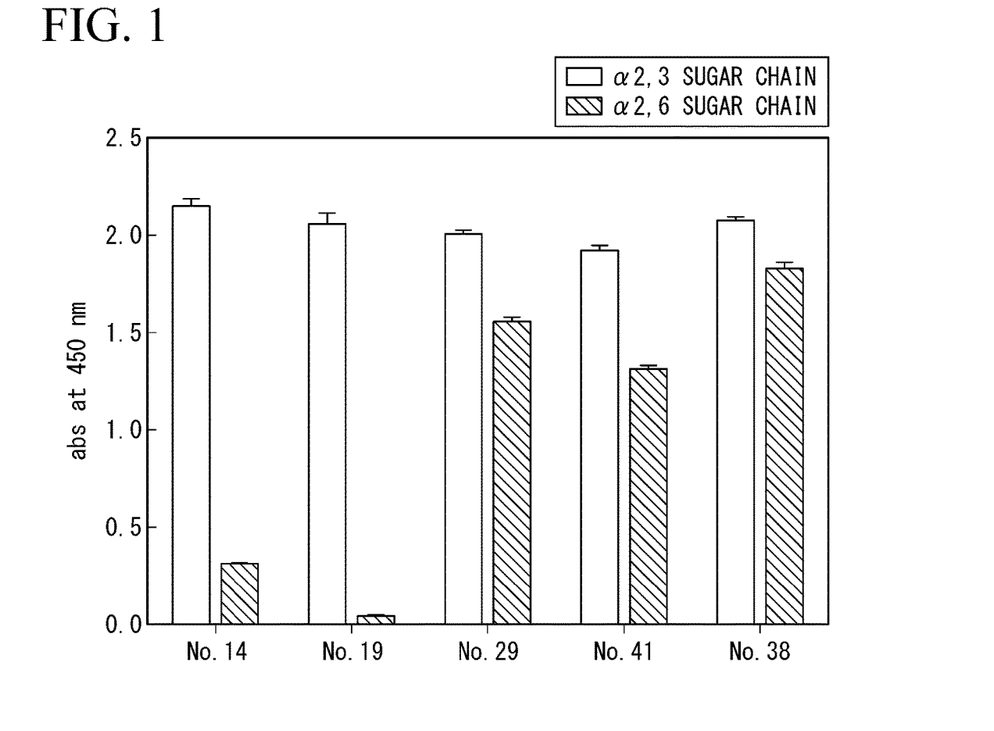
FIG. 1 is a graph showing the results of confirming the binding property of an antibody obtained in Example 1 to an α2,3 sugar chain and a sugar chain in which a terminal sialic acid residue is bonded to galactose by an α2,6 bond (hereinafter, also referred to as an α2,6 sugar chain) by ELISA.

A rabbit (slc: JW/CSK, 13 weeks old) was immunized using Siaα2-3Galβ1-4GlcNAc-BSA as an immunogen, and for the obtained rabbit B cells, a test of binding the cell (a single cell) to Siaα2-3Galβ1-4GlcNAc was carried out by an ELISA, and 56 positive clones were selected. Antibody genes were obtained from the selected positive clones by single cell PCR. Each of the obtained antibody gene sequences was transfected into human embryonic kidney cells 293, and the recombinant rabbit antibody secreted into the culture supernatant was subjected to the following ELISA to check the binding property to the α2,3 sugar chain and the α2,6 sugar chain, thereby obtaining two antibodies (Nos. 14 and 19) having a high binding property to the α2,3 sugar chain and a low binding property to the α2,6 sugar chain. FIG. 1 shows the results of the ELISA test of these two antibodies. It is to be noted that as a control, the results of the three antibodies (Nos. 29, 41, and 38) not selected above are also shown together.

Binding Property to α2,3 Sugar Chain

50 µl of a Siaα2-3Gal antigen BSA-MBS-peptide conjugate (BSA-MBS-sialic acid α(2,3)β1,4GlcNAc) was added to a 96-well plate at 1 µl/ml (×2,500) and incubated at 37° C. for 1 hour to immobilize the antigen on the well of the plate. After washing 3 times with phosphate-buffered saline (PBS) containing 0.1% Tween 20 (PBST), 100 µl of 1% BSA/PBS was added thereto, and shaking was carried out overnight at 4° C. to carry out blocking. After washing 3 times with PBST, 50 µl of the culture supernatant of each clone obtained in Example 1 diluted 2-fold was added thereto, and shaking was carried out at room temperature for 1 hour. After washing 3 times with PBST, 50 µl of an anti-Rabbit IgG HRP (×10,000; ab97080, manufactured by abcam, plc) was added thereto, and shaking was carried out at room temperature for 1 hour. After washing with PBST three times, 100 µl/well of a TMB substrate solution (composition: 3,3',5,5'-tetramethylbenzidine, catalog number: N301, manufactured by Thermo Fisher Scientific, Inc.) was added thereto and incubated for 5 minutes. Next, 100 µl/well of 0.1 N HCl was added thereto, and the absorbance at 450 nm was measured.

Binding Property to α2,6 Sugar Chain

The same procedure as above was carried out except that a Siaα2,6Gal antigen BSA-MBS-peptide conjugate was used instead of the Siaα2,3Gal antigen BSA-MBS-peptide conjugate, and the absorbance at 450 nm was measured.

Example 2

The KD values of the No. 14 antibody and No. 19 antibody obtained in Example 1 were calculated as follows.

An amino reactive biosensor (AR2G; manufactured by FORTEBIO Inc.) was subjected to hydrophilization with ultrapure water and immersed in a 20 µg/mL BSA-MBS-sialic acid α(2,3)β1,4GlcNAc antigen solution or a BSA-MBS-sialic acid α(2,3)β1,4GlcNAc antigen solution for 10 minutes to immobilize each antigen on the sensor. The sensor was immersed in an EDC-/sNHS solution (composition: mixture of 1-ethyl-3-(3-dimethylaminopropyl)carbodiimide (manufactured by FORTEBIO Inc.) and sulfo-N-hydroxysuccinimide (manufactured by FORTEBIO Inc.) in a ratio of 1:1) to carry out blocking. A BSA-MBS-β1,4GlcNAc antigen-immobilized biosensor was prepared by immersing the sensor in a sialidase solution (composition: 3 µL of α(2→3,6,8,9) Neuraminidase from Arthrobacter ureafaciens (N3786-1SET, manufactured by Sigma-Aldrich Co. LLC)+47 µL of 100 mM an acetate buffer (pH 5.5)) at 37° C. for 3 hours after blocking to release sialic acid. After washing with PBS, the biosensor was immersed in each antibody solution of 3.75 to 60 nM for 300 seconds under the condition of 30° C., and the binding state of the antibody to the antigen was measured. Then, it was immersed in PBS for 300 seconds, and the dissociation state of the antibody from the antigen was measured. The change in the wavelength shift Δλ caused by the change in the number of antibodies bound to the biosensor or the number of antibodies dissociated from the biosensor was measured in real time to generate a reaction profile on an Octet system (manufactured by FORTEBIO Inc.). KD values were calculated from the sensorgrams of binding and dissociation obtained in antibody solutions at concentrations of 3.75 nM to 60 nM. The calculated KD values are shown in Table 3. In addition, the results of the above sensorgrams of the No. 14 antibody and No. 19 antibody are each shown in FIG. 2A to FIG. 2C and FIG. 3A to FIG. 3C.

Comparative Example 1

Figure 4A:
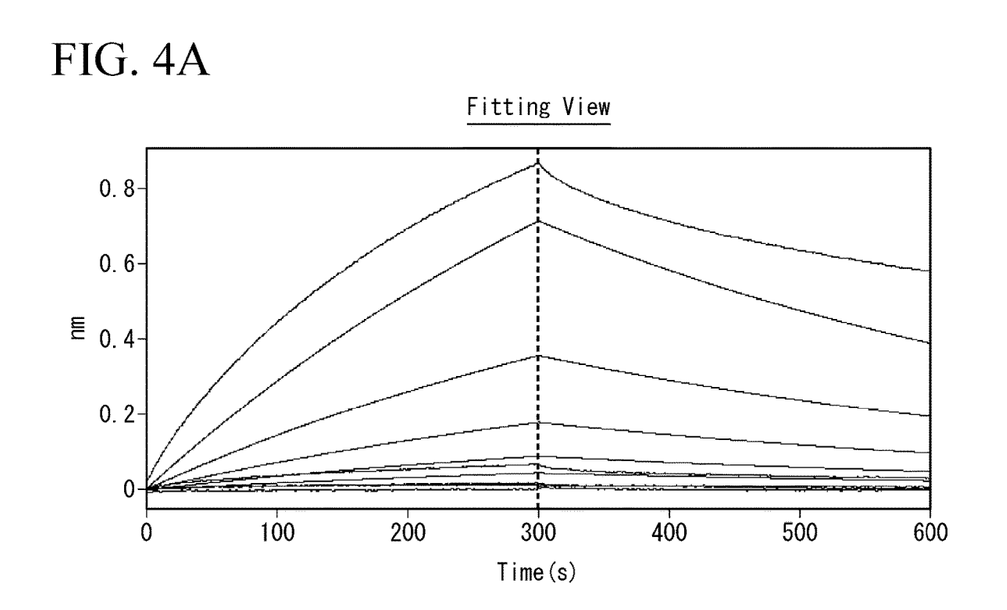
FIG. 4A is a graph showing the results of a sensorgram of an HYB4 antibody to a biosensor on which an α2,6 sugar chain is immobilized, in Comparative Example 1.
Figure 4B:
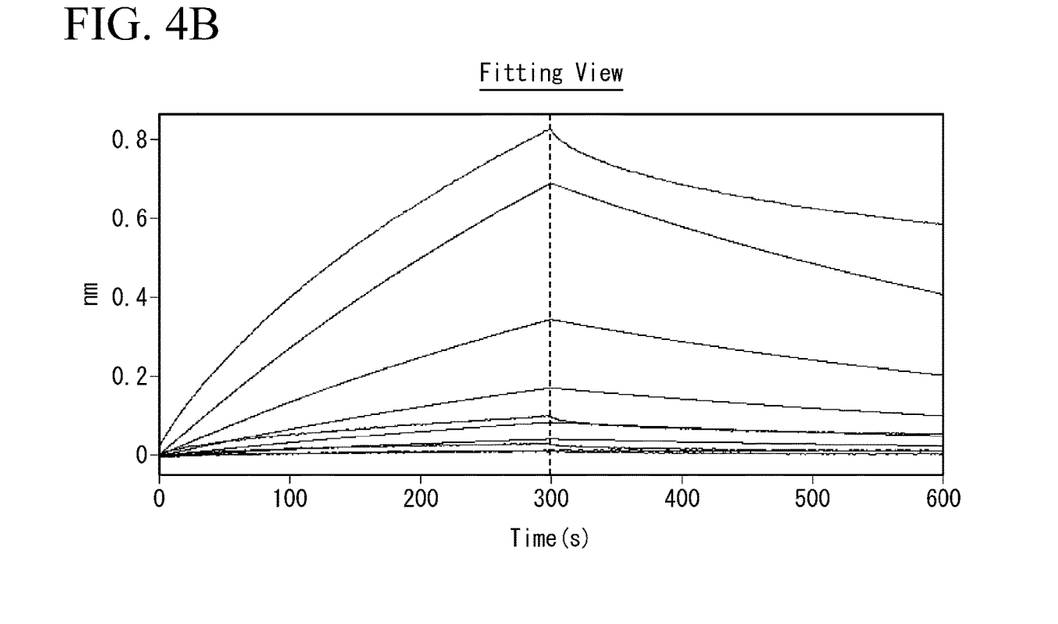
FIG. 4B is a graph showing the results of a sensorgram of an HYB4 antibody to a biosensor on which an α2,3 sugar chain is immobilized, in Comparative Example 1.
Figure 4C:
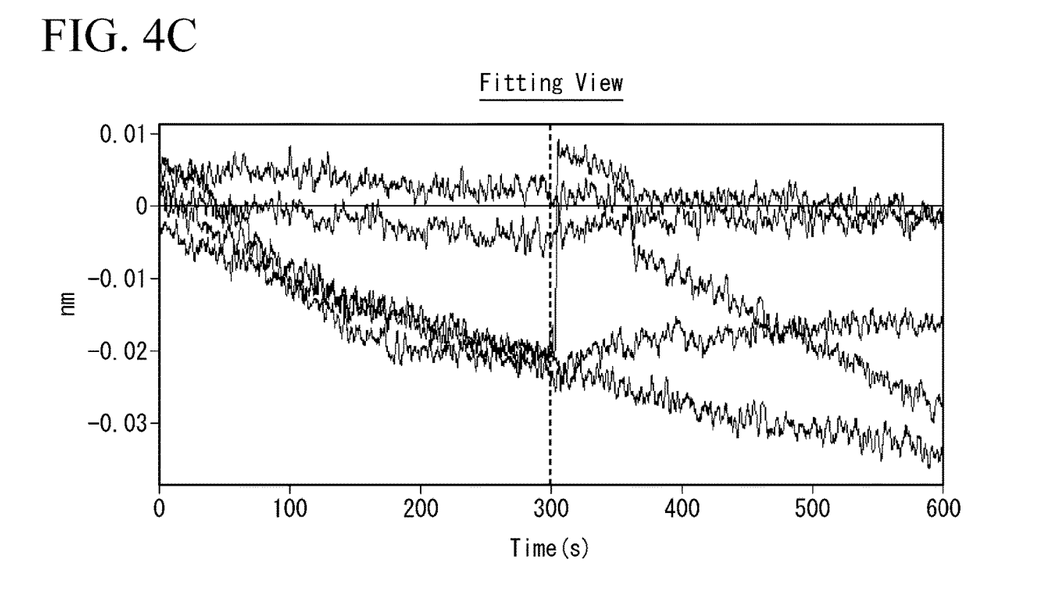
FIG. 4C is a graph showing the results of a sensorgram of an HYB4 antibody to a biosensor on which a galactose-bonded sugar chain is immobilized, in Comparative Example 1.

The KD value was calculated in the same manner as in Example 2 except that an HYB4 antibody (manufactured by FUJIFILM Wako Pure Chemical Corporation), which is a known mouse anti-α2,3 sugar chain monoclonal antibody, was used instead of the No. 14 antibody and the No. 19 antibody. The KD value of the HYB4 antibody is shown in Table 3, and the results of the sensorgram of the HYB4 antibody are shown in FIG. 4A to FIG. 4C.

TABLE 3

| Antibody name | KD value (M) with α2,3 sugar chain | KD value (M) with α2,6 sugar chain | KD value (M) with galactose-bonded sugar chain |
|---|---|---|---|
| No. 14 | $2.7 \times 10^{-8} \pm 3.9 \times 10^{-9}$ | $9.1 \times 10^{-9} \pm 2.5 \times 10^{-24}$ | $9.8 \times 10^{-5} \pm 00$ |
| No. 19 | $1.6 \times 10^{-8} \pm 1.9 \times 10^{-15}$ | $6.3 \times 10^{-6} \pm 1.6 \times 10^{-19}$ | N.D |
| HYB4 | $8.6 \times 10^{-6} \pm 1.6 \times 10^{-4}$ | $1.4 \times 10^{-5} \pm 1.4 \times 10^{-2}$ | N.D |

N.D: not detected

Figure 2A:
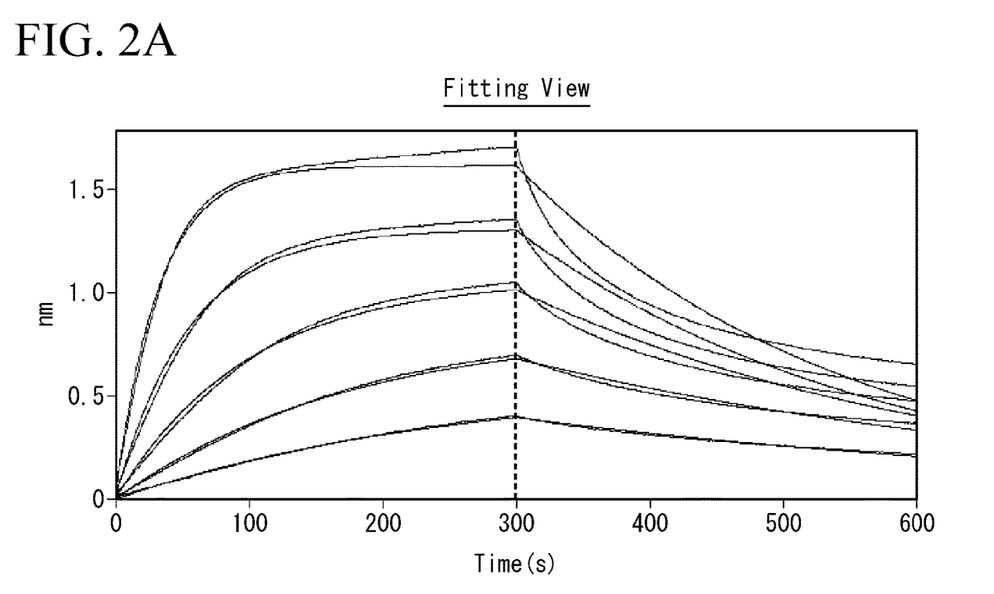
FIG. 2A is a graph showing the results of a sensorgram of a No. 14 antibody to a biosensor on which an α2,6 sugar chain is immobilized, in Example 2.
Figure 2B:
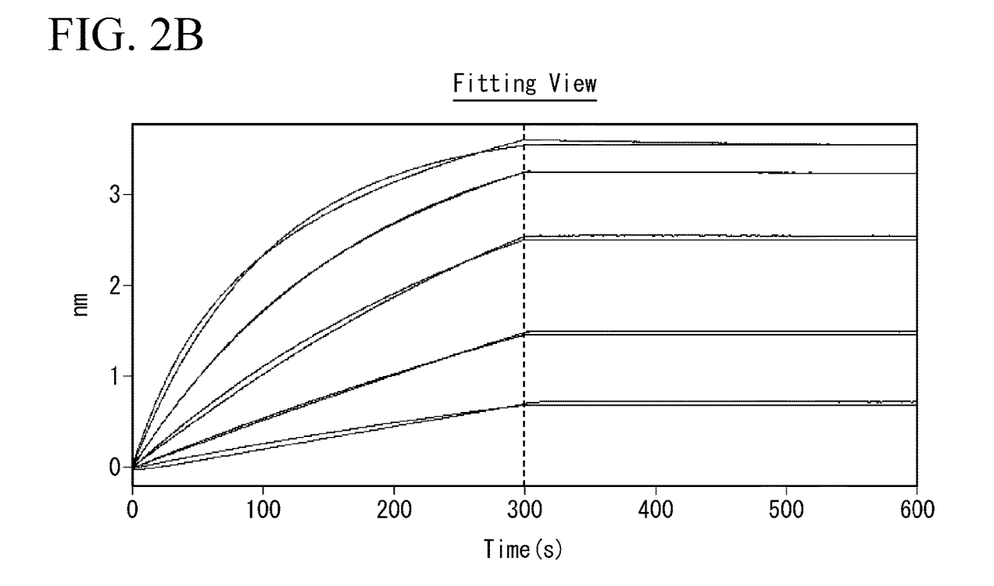
FIG. 2B is a graph showing the results of a sensorgram of a No. 14 antibody to a biosensor on which an α2,3 sugar chain is immobilized, in Example 2.
Figure 2C:
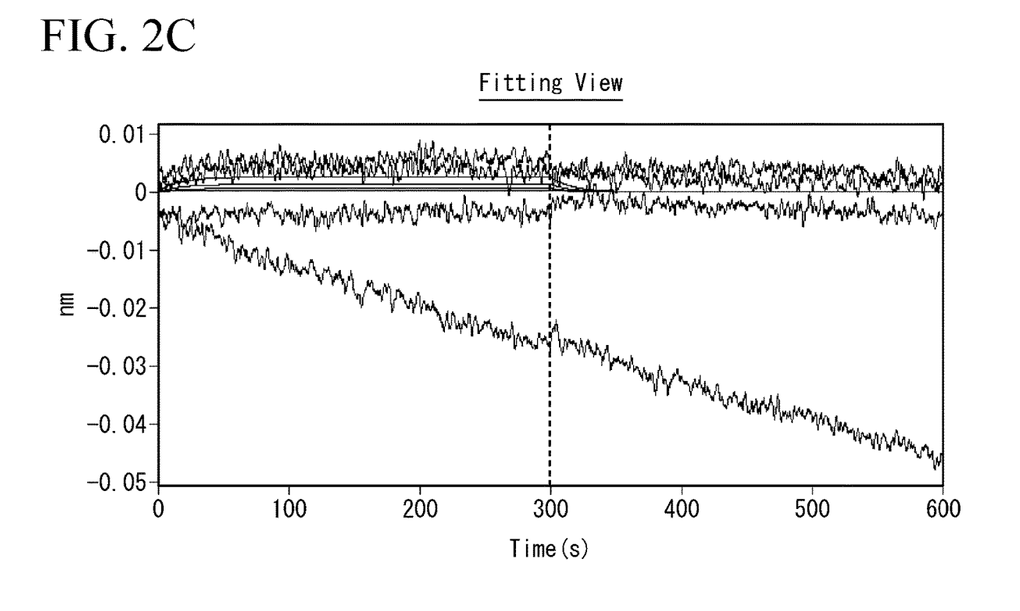
FIG. 2C is a graph showing the results of a sensorgram of a No. 14 antibody to a biosensor on which a sugar chain in which galactose to which sialic acid is not bonded is bonded to a terminal (hereinafter, also referred to as a galactose-bonded sugar chain) is immobilized, in Example 2.

As shown in Table 3, the results were such that the KD value of the No. 14 antibody with the α2,3 sugar chain was $2.7 \times 10^{-8} \pm 3.9 \times 10^{-9}$, which was higher by 33.7 times than the dissociation constant KD value with the α2,6 sugar chain of $9.1 \times 10^{-9} \pm 2.5 \times 10^{-24}$. However, it was revealed that as shown in FIG. 2A, the No. 14 antibody was rapidly dissociated from the α2,6 sugar chain after binding thereto, whereas it was not dissociated from the α2,3 sugar chain after once binding thereto as shown in FIG. 2B. Further, as shown in FIG. 2C, no binding to the galactose-bonded sugar chain was observed. As a result, it was revealed that in a case where the α2,3 sugar chain is present, the α2,6 sugar chain bound to the No. 14 antibody was replaced with the α2,3 sugar chain, and thus the No. 14 antibody is an antibody having a high binding property to the α2,3 sugar chain.

Figure 3A:
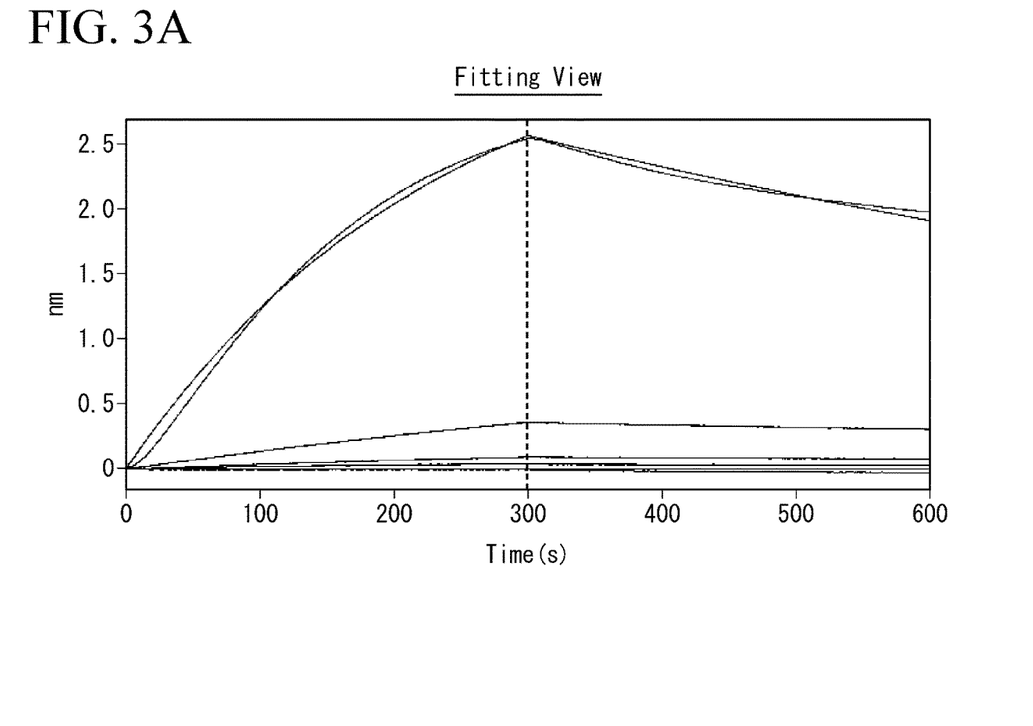
FIG. 3A is a graph showing the results of a sensorgram of a No. 19 antibody to a biosensor on which an α2,6 sugar chain is immobilized, in Example 2.
Figure 3B:
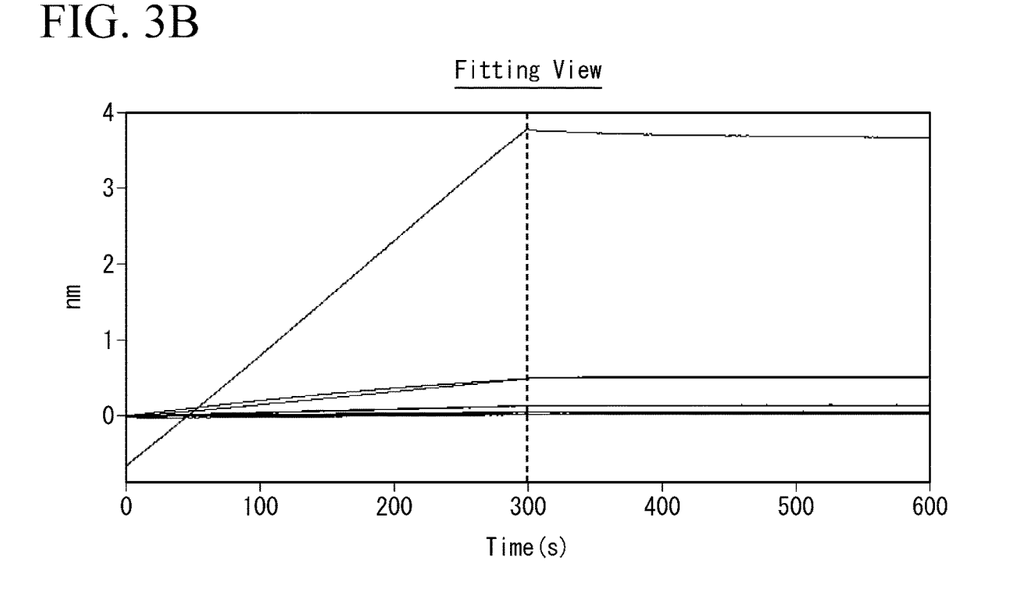
FIG. 3B is a graph showing the results of a sensorgram of a No. 19 antibody to a biosensor on which an α2,3 sugar chain is immobilized, in Example 2.
Figure 3C:
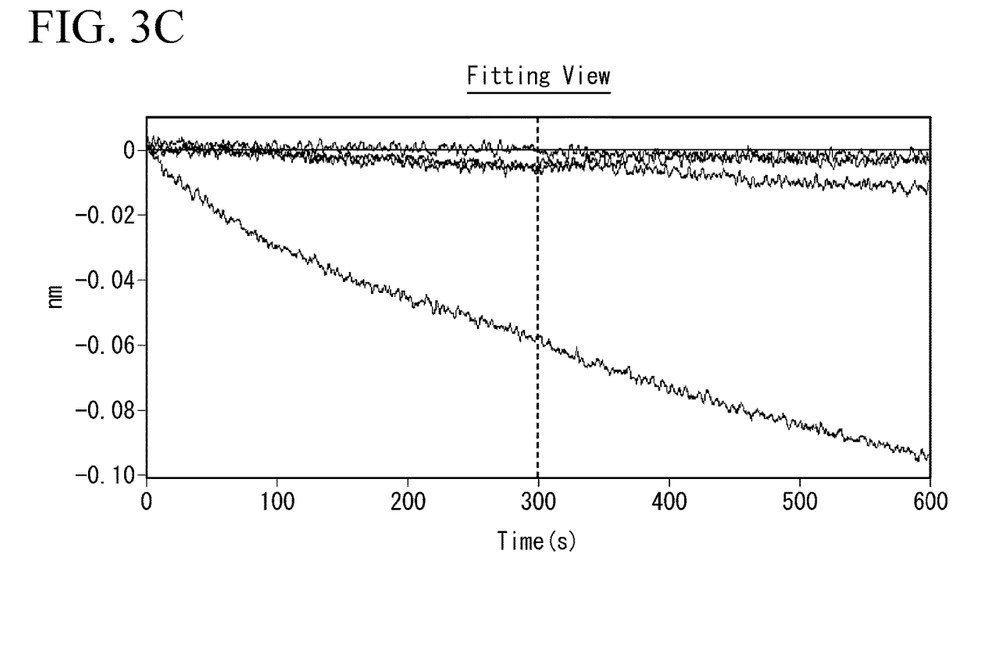
FIG. 3C is a graph showing the results of a sensorgram of a No. 19 antibody to a biosensor on which a galactose-bonded sugar chain is immobilized, in Example 2.

In addition, the results were such that the KD value of the No. 19 antibody with the α2,3 sugar chain was $1.6 \times 10^{-8} \pm 1.9 \times 10^{-15}$, which was lower by 25.4 times than the KD value with the α2,6 sugar chain of $6.3 \times 10^{-6} \pm 1.6 \times 10^{-19}$. Further, as shown in FIG. 3C, no binding to the galactose-bonded sugar chain was observed. Further, as shown in FIG. 3A, the No. 19 antibody was rapidly dissociated from the α2,6 sugar chain after binding thereto, whereas it was not dissociated from the α2,3 sugar chain after once binding thereto as shown in FIG. 3B. From these results, it was revealed that the No. 19 antibody is an antibody having a high binding property to the α2,3 sugar chain.

On the other hand, the KD value of the HYB4 antibody with the α2,3 sugar chain was $8.6 \times 10^{-6} \pm 1.6 \times 10^{-4}$, which was 31.4 times the KD value of the No. 14 antibody and 18.6 times the KD value of the No. 19 antibody. Further, as shown in FIG. 4B, the HYB4 antibody was rapidly dissociated from the α2,3 sugar chain in a case where it was immersed in PBS after binding to the α2,3 sugar chain.

From the above results, it was confirmed that the HYB4 antibody has a low binding property to the α2,3 sugar chain as compared with the No. 14 antibody and the No. 19 antibody.

INDUSTRIAL APPLICABILITY

According to the present invention, a monoclonal antibody or an antibody fragment thereof, having a high binding property to an α2,3 sugar chain, and a measurement method for an α2,3 sugar chain are provided.

The invention claimed is:

1. A monoclonal antibody or the antibody fragment thereof, wherein an amino acid sequence of a complementarity-determining region (CDR) 1 (CDR1) of a heavy chain variable region (VH) of the antibody or the antibody fragment thereof comprises the amino acid sequence set forth in SEQ ID NO:1, an amino acid sequence of CDR2 of the VH comprises the amino acid sequence set forth in SEQ ID NO:2, an amino acid sequence of CDR3 of the VH comprises the amino acid sequence set forth in SEQ ID NO:3, an amino acid sequence of CDR1 of a light chain variable region (VL) comprises the amino acid sequence set forth in SEQ ID NO:4, an amino acid sequence of CDR2 of the VL comprises the amino acid sequence set forth in SEQ ID NO:5, and an amino acid sequence of CDR3 of the VL comprises the amino acid sequence set forth in SEQ ID NO:6.

2. The monoclonal antibody or the antibody fragment thereof of claim 1, wherein an amino acid sequence of the VH of the antibody or the antibody fragment thereof comprises the amino acid sequence set forth in SEQ ID NO:13, and an amino acid sequence of the VL comprises the amino acid sequence set forth in SEQ ID NO:14.

3. A monoclonal antibody or the antibody fragment thereof, wherein an amino acid sequence of CDR1 of the VH of the antibody or the antibody fragment thereof comprises the amino acid sequence set forth in SEQ ID NO:7, an amino acid sequence of CDR2 of the VH comprises the amino acid sequence set forth in SEQ ID NO:8, an amino acid sequence of CDR3 of the VH comprises the amino acid sequence set forth in SEQ ID NO:9, an amino acid sequence of CDR1 of the VL comprises the amino acid sequence set forth in SEQ ID NO:10, an amino acid sequence of CDR2 of the VL comprises the amino acid sequence set forth in SEQ ID NO:11, and an amino acid sequence of CDR3 of the VL comprises the amino acid sequence set forth in SEQ ID NO:12.

4. The monoclonal antibody or the antibody fragment thereof of claim 3, wherein an amino acid sequence of the VH of the antibody or the antibody fragment thereof comprises the amino acid sequence set forth in SEQ ID NO:15 and an amino acid sequence of the VL comprises the amino acid sequence set forth in SEQ ID NO:16.

* * * * *